United States Patent [19]

Howarth et al.

[11] 4,207,235

[45] Jun. 10, 1980

[54] SELECTIVE EPOXIDATION OF STEROIDAL BROMOHYDRINS

[75] Inventors: George B. Howarth, Springfield, Mo.; Richard D. Stacy, Boulder, Colo.

[73] Assignee: Syntex (U.S.A.) Inc., Palo Alto, Calif.

[21] Appl. No.: 2,820

[22] Filed: Jan. 12, 1979

[51] Int. Cl.² ............................................. C07J 71/00
[52] U.S. Cl. ............................................. 260/239.55 R
[58] Field of Search ............................... 260/239.55 R

[56] References Cited

U.S. PATENT DOCUMENTS

| | | | |
|---|---|---|---|
| 3,684,800 | 8/1972 | Irmscher et al. | 260/397.45 |
| 3,980,778 | 9/1976 | Ayer et al. | 424/243 |

*Primary Examiner*—Elbert L. Roberts
*Attorney, Agent, or Firm*—Tom M. Moran; Gerard A. Blaufarb

[57] ABSTRACT

Vicinal steroidal epoxides are prepared by reacting the corresponding vicinal steroidal bromohydrin with a heterocyclic base such as 1,5-diazabicyclo[4.3.0]non-5-ene or 1,5-diazabicyclo[5.4.0]-undec-5-ene.

24 Claims, No Drawings

SELECTIVE EPOXIDATION OF STEROIDAL BROMOHYDRINS

BACKGROUND OF THE INVENTION

This invention relates to a process for selectively epoxidizing steroidal bromohydrins and is particularly valuable where the steroid being epoxidized also has a C-21 acyloxy group.

PRIOR ART

In the preparation of vicinal steroidal epoxides, it is generally known that the bromohydrin can be converted to the epoxide by the use of a base such as sodium hydroxide or potassium carbonate. However, if a C-21 acyloxy group is present during the epoxidation, it is cleaved to form the corresponding C-21 hydroxy. Where the C-21 acyloxy is desired this results in the need to re-acetylate the C-21 hydroxy group.

It is also known that certain heterocyclic bases such as 1,5-diazabicyclo[4.3.0]non-5-ene (hereafter DBN) or 1,5-diazabicyclo[5.4.0]undec-5-ene (hereafter DBU) have been used for the dehydrohalogenation of organic halocarbons. See, for example, German Pat. No. 1,186,063 issued Jan. 28, 1965; German Pat. No. 1,279,679 issued Oct. 10, 1968; Japanese Kokai 74 72,248 and Hughes NA, CARBOHYD. RES., 25 (1), 242-5 (1972).

SUMMARY OF THE INVENTION

Surprisingly, it has now been found that vicinal steroidal bromohydrins where the bromo group is not situated at a position β to a carbonyl group can be converted to the corresponding vicinal steroidal epoxide by reacting the bromohydrin with a heterocyclic base such as DBN or DBU in a suitable solvent, preferably at temperatures of about 5° to 100° C. The process is particulary useful in treating steroids having a C-21 acyloxy group, because that group is not affected by the reaction.

FURTHER DISCUSSION AND PREFERRED EMBODIMENTS

The bromohydrins which are useful as starting materials in the process of this invention are any steroids wherein a bromine and a hydroxy are at any two adjacent positions on the steroid nucleus, that is a vicinal steroidal bromohydrin, and wherein the bromine is not situated β to a carbonyl group. Preferred are the trans bromohydrins, e.g. 9α,11β- or 14α, 15β- bromohydrins. Particularly preferred are the 9α,11β-bromohydrins of Formula (I)

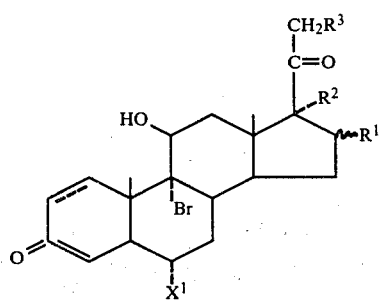

wherein $X^1$ is hydrogen, fluoro or chloro;
$R^1$ is hydrogen, α-methyl or β-methyl when
$R^2$ is hydroxy or acyloxy of 2-12 carbon atoms or
$R^1$ and $R^2$ together are 16α,17α-isopropylidenedioxy;
$R^3$ is an acyloxy group of 2-12 carbon atoms; and
the dotted line between C-1 and C-2 represents an optional additional bond.

Representative compounds include
6α-fluoro-9α-bromo-11β,17α-dihydroxy-16α-methyl-21-acetoxypregna-1,4-diene-3,20-dione;
6α-fluoro-9α-bromo-11β,17α-dihydroxy-16β-methyl-21-acetoxypregna-1,4-diene-3,20-dione;
6α-chloro-9α-bromo-11β,17α-dihydroxy-16α-methyl-21-acetoxypregna-1,4-diene-3,20-dione;
9α-bromo-11β,17α-dihydroxy-16α-methyl-21-acetoxypregna-1,4-diene-3,20-dione;
6α-fluoro-9α-bromo-11β-hydroxy-16α-17α-isopropylidenedioxy-21-acetoxypregna-1,4-diene-3,20-dione;
6α-chloro-9α-bromo-11β-hydroxy-16α-17α-isopropylidenedioxy-21-acetoxypregna-1,4-diene-3,20-dione;
9α-bromo-11β-hydroxy-16α-17α-isopropylidenedioxy-21-acetoxypregna 1,4-diene-3,20-dione;
other corresponding 21-acyloxy steroids;
other corresponding 17 acyloxy compounds; and the like.

An acyloxy group is one having the formula $R^4C(O)O$— where $R^4$ is alkyl of 1-11 carbon atoms, e.g., methyl, ethyl, propyl, butyl, hexyl, nonyl, and the like.

The compounds are converted into the corresponding epoxides (for example a 9α-bromo-11β-hydroxy steroid gives a 9β,11β-epoxide) which are useful as intermediates in the preparation of anti-inflammatory steroids.

The process of this invention comprises reactively contacting any of the steroids mentioned above with a heterocyclic base of Formula (II)

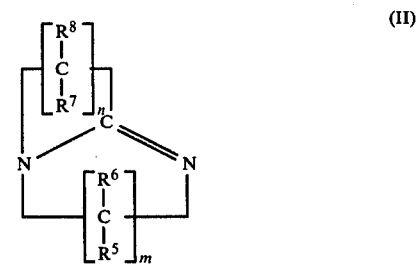

wherein $R^5$, $R^6$, $R^7$ and $R^8$ are independently hydrogen or alkyl of 1-4 carbon atoms, n is an integer of 2 through 7 and m is an integer of 2 through 4. Of these, the compounds wherein $R^1$, $R^2$, $R^3$ and $R^4$ are each hydrogen are preferred and the compounds wherein m is 3 and n is 3, 4 or 5 are very preferred. The most preferred are the the compounds DBN ($R^5$, $R^6$, $R^7$ and $R^8$ are all hydrogen; n is 3; and m is 3) and DBU ($R^5$, $R^6$, $R^7$ and $R^8$ are all hydrogen; n is 5; and m is 3).

The process can be continuous or batch and comprises reactively contacting a steroidal bromohydrin, e.g. one represented by Formula (I) wherein $X^1$, $R^1$, $R^2$ and $R^3$ are hereinbefore defined, with a base represented by Formula (II) at low temperatures for a time sufficient to form the desired steroidal epoxide. The time needed for complete conversion will vary in part with the temperature. At higher temperatures, less time is required. Generally, the reaction will be complete in five hours or less, and usually less than one hour is required at room temperature. The temperature may be between 5° C. and 100° C., but generally will be less than 50° C. and preferably will be at ambient temperature, i.e., 20°-25° C.

Generally the reaction is carried out in a compatible liquid organic solvent which is preferably a dipolar, aprotic solvent. Representative solvents include tetrahydrofuran, dioxan, dimethyl sulfoxide, acetonitrile and substituted or unsubstituted alkyl amides. Dimethylformamide has been found to be particularly valuable and is therefore preferred. Preferably, the reaction is run as a batch type reaction while the reaction mixture is stirred vigorously.

Another aspect of this invention is a process which comprises (a) reactively contacting a steroidal vicinal bromohydrin wherein the bromo group is not situated β to a carbonyl with a heterocyclic base of Formula (II), as defined hereinbefore, to form the corresponding vicinal steroidal epoxide and (b) converting the resulting epoxide to a fluorohydrin. Step (a) has been fully discussed hereinbefore, while the conversion of step (b) may be performed using any means which are readily available in the art as discussed hereafter. The two-step process is particularly valuable in the preparation of 9α,11β-fluorohydrins such as the 21-acetoxy derivative flumethasone (6α,9α-difluoro-11β,17α-dihydroxy-16α-methyl-21-acetoxypregna-1,4-diene-3,20-dione) and fluocinonide (6α,9α-difluoro-11β-hydroxy-16α,17α-isopropylidenedioxy-21-acetoxypregna-1,4-diene-3,20-dione) and is best represented by the following reaction sequence:

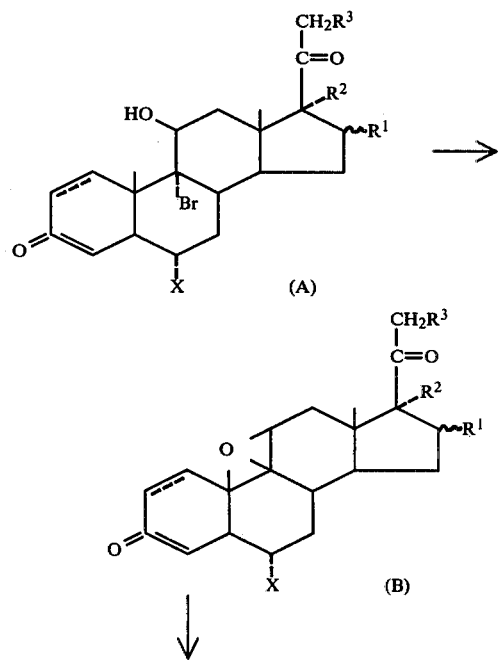

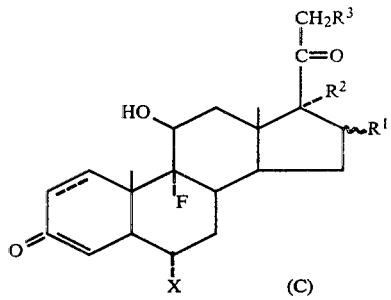

wherein X, $R^1$, $R^3$ and the broken line between C-1 and C-2 have the meanings set forth hereinbefore. In the process for preparing flumethasone, X is fluoro, $R^1$ is α-methyl, $R^2$ is α-hydroxy, $R^3$ is acetoxy and there is a double bond between C-1 and C-2. In the process for preparing fluocinonide X is fluoro, $R^1$ and $R^2$ together are 16α,17α-isopropylidenedioxy, $R^3$ is acetoxy and there is a double bond between C-1 and C-2. When $R^3$ in Formula (C) is an acyloxy such as acetoxy, it may subsequently and optionally be hydrolyzed using a suitable base to form the 21-hydroxy compound.

The fluorination step (b) of the two step process of this invention may be carried out using procedures which are known in the art. For example, the 9β,11β-epoxide may be reacted with hydrofluoric acid in chloroform free of ethanol as taught by Fried and Sabo (J. Am. Chem. Soc., 76, 1455, 1954) or with the addition of a Lewis base such as tetrahydrofuran as taught by Hirschman, et al. (J. Am. Chem. Soc. 78, 4957, 1956). These reactions are run at low temperatures such as −30° to −60° C. Of more commercial value is the reaction of the 9β,11β-epoxide with hydrofluoric acid in anhydrous dimethylformamide (see U.S. Pat. No. 3,007,923 to Muller et al. of Les Labortories Francais de Chimiotherapie) or in a carbamic or thiocarbamic acid or amide or ester of such an acid (see U.S. Pat. No. 3,211,758 to Tarkoey of Ciba-Geigy) or other solvents such as dimethylacetamide. All of the foregoing references are incorporated herein by reference.

Fluorination effected with anhydrous hydrofluoric acid dissolved in dimethylformamide at temperatures between about −10° and about 10° C. is preferably conducted using hydrofluoric acid in excess of the steroid reactant although varying amounts may be employed. An amount of dimethylformamide about equal in volume to the amount of liquefied, anhydrous hydrofluoric acid is advantageously employed, although the amount of dimethylformamide may be more or less than the hydrofluoric acid.

The reaction can occur either by (a) dissolving anhydrous hydrofluoric acid in dimethylformamide at a low temperature and immediately thereafter introducing the epoxy steroid to effect the fluorination at temperatures between −10° and 10° C. or (b) more advantageously for industrial utilization, by dividing the reaction into the steps of preparing the fluorination reagent first by introducing the anhydrous hydrofluoric acid into the dimethylformamide at temperatures between 40° C. and 60° C. and thereafter cooling the mixture and introducing the epoxy steroid. From the latter alternative procedure, a stable fluorination reagent is thus obtained which may be stored and which is available for fluorination at any time. The process for the preparation of this reagent preferably consists of introducing the anhydrous hydrofluoric acid into the dimethylformamide at a temperature between 40° and 60° C. In order to carry out the fluorination, the subsequent procedure is the same as that described above, namely introducing the 9β,11β-epoxy steroid into the cooled solution of the reagent.

The aforementioned carbamic acid or thiocarbamic acid compounds of the Tarkoey U.S. Pat. No. 3,211,758 are, for example, the free carbamic or thiocarbamic acids or their esters, as well as their derivatives alkylated at the nitrogen atom, more especially N,N-dimethyl-, N,N-diethyl-, N-monomethyl-, N-monoethylcarbamic or -thiocarbamic acid. Particularly suitable esters of these compounds are: Lower alkyl esters, for example methylurethane, ethylurethane, isopropylurethane or the like. Furthermore, there may be used with advantage amides of the aforementioned carbamic or thiocarbamic acids, such as urea, thiourea, N-mono-, di-, tri- or tetra-lower alkyl ureas, for example, tetramethyl urea, symmetrical dimethylurea, dimethylthiourea or the like.

When carbonic acid derivatives are mixed with anhydrous hydrogen fluoride, preferably with liquid hydrogen fluoride, they are transformed into colorless, storable liquids which fume very little. The mixing of the hydrogen fluoride and the carbonic acids or their derivatives is best performed at an elevated temperature, preferably between 30° and 70° C., and the ratio of the quantities of the carbonic acid/derivative and the hydrogen fluoride is generally within the range of about 0.65 to 1.7, preferably 0.8 to 1.7.

The present process can be performed within a temperature interval which is very wide compared with that required in similar, known methods. Thus, the epoxide ring itself can be opened up at 20° to 30° C. with the obtention of a pure vicinal 9α-fluoro-11β-hydroxy-steroid in a very good yield. Moreover, several of the carbonic acid derivatives (for example, urea) are inexpensive and very pure. In addition, many of them are solid and can thus be dried more easily than the liquid solvents just mentioned.

The following examples give representative conditions under which the process of this invention can be carried out. It will be understood, however, that these examples are not intended to limit the scope of the subject matter claimed herein. On the contrary, it is intended that all reasonable alternatives, modifications and equivalents are to be included within the spirit and scope of the invention set forth in the appended claims.

EXAMPLE 1

Preparation of 6α-fluoro-9β,11β-oxido-16α-methyl-17α-hydroxy-21-acetoxypregna-1,4-diene-3,20-dione.

A solution of 100 grams (g) 6α-fluoro-9α-bromo-11β,17α-dihydroxy-16α-methyl-21-acetoxypregna-1,4-diene-3,20-dione in 700 milliliters (ml) of dry dimethylformamide is prepared and 35 ml of DBU was added thereto. The resulting solution is stirred at ambient temperature for 45 minutes followed by addition of acetic acid to neutralize any additional base. The reaction mixture is poured into water and the precipitate isolated by filtration to give 82 grams of 6α-fluoro-9β,11β-oxido-16α-methyl-17α-hydroxy-21-acetoxypregna-1,4-diene-3,20-dione, m.p. 220°–223° C.

EXAMPLE 2

Preparation of 6α-fluoro-9β,11β-oxido-16α-methyl-17α-hydroxy-21-acetoxypregna-1,4-diene-3,20-dione.

One hundred (100) g of 6α-fluoro-9α-bromo-11β,17α-dihydroxy-16α-methyl-21-acetoxypregna-1,4-diene-3,20-dione is dissolved in 700 ml of dry dimethylformamide. Thirty-two (32) ml of DBN are added thereto and the resulting solution is stirred at ambient temperature for 45 minutes, whereupon 20 ml of acetic acid are added. The reaction mixture is poured into water and the resulting precipitate is isolated by filtration to yield 82.2 grams of 6α-fluoro-9β,11β-oxido-16α-methyl-17α-hydroxy-21-acetoxypregna-1,4-diene-3,20-dione, m.p. 220°–223° C.

EXAMPLE 3

Preparation of 6α-fluoro-9β,11β-oxido-16α,17α-isopropylidenedioxy-21-acetoxypregna-1,4-diene-3,20-dione.

A solution of 6α-fluoro-9α-bromo-11βhydroxy-16α,17α-isopropylidenedioxy-21-acetoxypregna-1,4-diene-3,20-dione is prepared by dissolving 55.5 grams of the compound in 500 ml of dry dimethylformamide. To this solution, 15 ml of DBU is added and the resulting solution is stirred at ambient temperature for 45 minutes followed by the addition of 15 ml acetic acid to neutralize any excess base. The resulting mixture is poured into water to give a precipitate which is then isolated by filtration to yield 46.2 grams of 6α-fluoro-9β,11β-oxido-16α,17α-isopropylidenedioxy-21-acetoxypregna-1,4-diene-3,20-dione, m.p. 233°–235° C.

EXAMPLE 4

Similarly, by following in principle the procedure of Examples 1 and 2, but substituting other appropriate 9α-bromo-11β-hydroxy steroids for 6α-fluoro-9α-bromo-11β,17α-dihydroxy-16α-methyl-21-acetoxypregna-1,4-diene-3,20-dione, such as 6α-fluoro-9α-bromo-11β,17α-dihydroxy-16α-methyl-21-isopropoxypregna-1,4-diene-3,20-dione;
6α-fluoro-9α-bromo-11β,17α-dihydroxy-16β-methyl-21-acetoxypregna-1,4-diene-3,20-dione;
6α-chloro-9α-bromo-11β,17α-dihydroxy-16α-methyl-21-acetoxypregna-1,4-diene-3,20-dione;
9α-bromo-11β,17α-dihydroxy-16α-methyl-21-acetoxypregna-1,4-diene-3,20-dione; and the like, other corresponding 9β,11β-epoxide steroids are prepared.

EXAMPLE 5

Similarly, by following in principle the procedure of Example 3, but substituting other appropriate 9α-bromo-11β-hydroxy steroids for 6α-fluoro-9α-bromo-11β-hydroxy-16α,17α,isopropylidenedioxy-21-acetoxypregna-1,4-diene-3,20-dione such as 6α-fluoro-9α-bromo-11β-hydroxy-16α-17-hydroxy-16α-isopropylidenedioxy-21-isopropoxypregna-1,4-diene-3,20-dione;
6α-chloro-9α-bromo-11β-hydroxy-16α-17α-isopropylidenedioxy-21-acetoxypregna-1,4-diene-3,20-dione;
9α-bromo-11β-hydroxy-16α-17α-isopropylidenedioxy-21-acetoxypregna 1,4-diene-3,20-dione; and the like, other corresponding 9β,11β-epoxide steroids are prepared.

EXAMPLE 6

To a stirred solution of 1.8 g of 6α-fluoro-9β,11β-oxido-16α-methyl-17α-hydroxy-21-acetoxypregna-1,4-diene-3,20-dione in 30 ml. of methylene chloride at 0° C., is added a cooled solution (−70° C.) of 2.11 g. anhydrous hydrogen fluoride in 3.7 ml. of tetrahydrofuran over a period of 20 minutes. The mixture is stirred at a temperature below 10° C. for 6 hours and then neutralized by the cautious addition of 5% aqueous sodium bicarbonate solution. The organic layer is separated, washed with water, dried over sodium sulfate and concentrated until solid forms. The cooled mixture is then filtered and the solid dissolved in hot ethyl acetate. This solution is filtered hot, then cooled and the solid which forms collected by filtration to yield 6α,9α-difluoro-11β,17α-dihydroxy-16α-methyl-21-acetoxypregna-1,4-diene-3,20-dione.

In a like manner, other 9β,11β-epoxide steroids prepared according to the procedures of Examples 3-5 are converted into the corresponding 9α-fluoro-11β-hydroxy steroids.

The subject matter claimed is:

1. Process for preparing a 9,11-epoxide which comprises reactively contacting a a compound represented by the formula

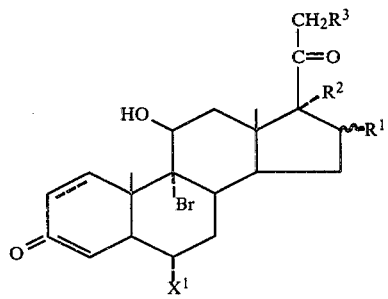

wherein
$X^1$ is hydrogen, fluoro or chloro;
$R^1$ is hydrogen, α-methyl or β-methyl when $R^2$ is hydroxy or acyloxy of 2-12 carbon atoms or $R^1$ and $R^2$ together are 16α,17α-isopropylidenedioxy;
$R^3$ is an acyloxy group of 2-12 carbon atoms; and
the dotted line between C-1 and C-2 represents an an optional additional bond with a compound represented by the formula

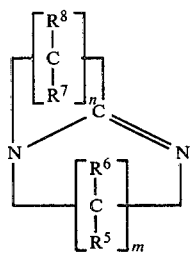

wherein $R^5$, $R^6$, $R^7$ and $R^8$ are independently hydrogen or alkyl of 1-4 carbon atoms, n is an integer of 2 through 7 and m is an integer of 2 through 4.

2. The process of claim 1 wherein $R^5$, $R^6$, $R^7$ and $R^8$ are all hydrogen.

3. The process of claim 2 wherein m is 3 and n is 3, 4 or 5.

4. The process of claim 3 wherein the compound represented by formula (II) is 1,5-diazabicyclo[4.3.0]-non-5-ene.

5. The process of claim 3 wherein the compound represented by formula (II) is 1,5-diazabicyclo[5.4.0]undec-5-ene.

6. The process of claim 1 wherein said steroidal bromohydrin is 6α-fluoro-9α-bromo-11β,17α-dihydroxy-16α-methyl-21-acetoxypregna-1,4-diene-3,20-dione.

7. The process of claim 1 wherein said steroidal bromohydrin is 6α-fluoro-9α-bromo-11β-hydroxy-16α,1-7α-isopropylidenedioxy-21-acetoxypregna-1,4-diene-3,20-dione.

8. The process of claim 1 wherein said process takes place in an aprotic, dipolar solvent.

9. The process of claim 8 wherein said process takes place in dimethylformamide.

10. A process for preparing a vicinal steroidal epoxide which comprises reactively contacting 1,5-diazabicyclo[4.3.0]non-5-ene or 1,5-diazabicyclo[5.4.0]undec-5-ene in dimethylformamide with a steroid of the formula

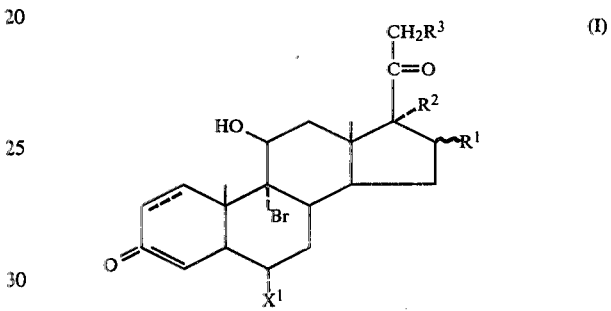

wherein
$X^1$ is hydrogen, fluoro or chloro;
$R^1$ is hydrogen, α-methyl or β-methyl;
$R^2$ is hydroxy or acyloxy of 2-12 carbon atoms;
$R^1$ and $R^2$ together are 16α,17α-isopropylidenedioxy;
$R^3$ is an acyloxy group of 2-12 carbon atoms; and
the dotted line between C-1 and C-2 represents an optional additional bond.

11. A process for preparing a 9α-fluoro-11β-hydroxypregn-4-ene which comprises (a) reactively contacting a a compound represented by the formula

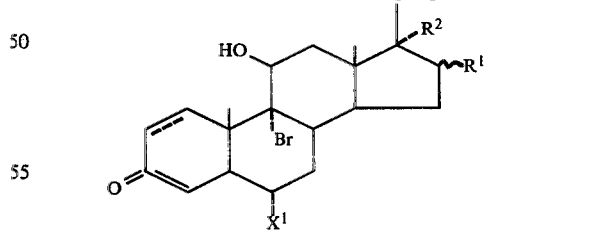

wherein
$X^1$ is hydrogen, fluoro or chloro;
$R^1$ is hydrogen, α-methyl or β-methyl when $R^2$ is hydroxy or acyloxy of 2-12 carbon atoms or $R^1$ and $R^2$ together are 16α,17α-isopropylidenedioxy;
$R^3$ is an acyloxy group of 2-12 carbon atoms; and
the dotted line between C-1 and C-2 represents an optional additional bond with a compound represented by the formula:

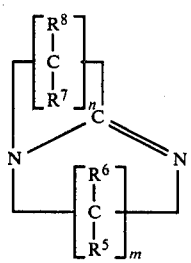 (II)

wherein $R^5$, $R^6$, $R^7$, and $R^8$ are independently hydrogen or alkyl of 1 through 4 carbon atoms, n is an integer of 2 through 7 and m is an integer of 2 through 4 to form a 9,11-epoxide and (b) fluorinating said 9,11-epoxide to form the desired 9α-fluoro-11β-hydroxypregna-4-ene.

12. The process of claim 11 wherein $R^5$, $R^6$, $R^7$ and $R^8$ are all hydrogen, m is 3 and n is 3, 4 or 5.

13. The process of claim 12 wherein the compound represented by formula (II) is 1,5-diazabicyclo[4.3.0]-non-5-ene.

14. The process of claim 12 wherein m is 3 and n is 5, namely 1,5-diazabicyclo[5.4.0]-undec-5-ene.

15. The process of claim 11 wherein said steroid is 6α-fluoro-9α-bromo-11β,17α-dihydroxy-16α-methyl-21-acetoxypregna-1,4-diene-3,20-dione.

16. The process of claim 11 wherein said steroid is 6α-fluoro-9α-bromo-11β-hydroxy-16α,17α-isopropylidenedioxy-21-acetoxypregna-1,4-diene-3,20-dione.

17. The process of claim 11, 12, 13 or 14 wherein step (a) is carried out in an aprotic, dipolar solvent.

18. The process of claim 11, 12, 13 or 14 wherein step (a) is carried out in dimethylformamide.

19. The process of claim 15 or 16 wherein the fluorinating agent is hydrogen fluoride in dimethylacetamide.

20. The process of claim 15 or 16 wherein the fluorinating agent is hydrogen fluoride in dimethylformamide.

21. The process of claim 15 or 16 wherein the fluorinating agent is hydrogen fluoride in a carbamic acid or thiocarbamic acid or a suitable amide or ester thereof.

22. The process of claim 15 or 16 wherein the fluorinating agent is hydrofluoric acid in urea.

23. The process of claim 11 wherein in step (a) said compound is represented by formula (I) wherein $X^1$ is fluoro, $R^1$ is α-methyl, $R^2$ is hydroxy, $R^3$ is acetoxy and there is a double bond between C-1 and C-2 and said compound represented by formula (II) is 1,5-diazabicyclo[4.3.0]non-5-ene or 1,5 diazabicyclo[5.4.0]undec-5-ene and in step (b) said fluorinating agent is hydrogen fluoride in urea, dimethylacetamide or dimethylformamide, and after step (b) is performed, said acetoxy at C-21 is converted to a hydroxy.

24. The process of claim 11 wherein in step (a) said is represented by formula (I) wherein $X^1$ is fluoro, $R^1$ and $R^2$ together are isopropylidenedioxy, $R^3$ is acetoxy and there is a double bond between C-1 and C-2 and said compound represented by formula (II) is 1,5-diazabicyclo[4.3.0]non-5-ene or 1,5 diazabicyclo[5.4.0]undec-5-ene and in step (b) said fluorinating agent is hydrogen fluoride in urea, dimethylacetamide or dimethylformamide, and after step (b) is performed, said acetoxy at C-21 is converted to a hydroxy.

* * * * *